United States Patent [19]

Kaiser et al.

[11] 4,089,961

[45] May 16, 1978

[54] ANTIPSYCHOTICALLY USEFUL QUINOLIZIDYLIDENE DERIVATIVES OF XANTHENES, THIOXANTHENES AND DIBENZOXEPINS

[75] Inventors: Carl Kaiser, Haddon Heights, N.J.; John Joseph Lafferty, Levittown, Pa.

[73] Assignee: SmithKline Corporation, Philadelphia, Pa.

[21] Appl. No.: 739,688

[22] Filed: Nov. 8, 1976

[51] Int. Cl.$^2$ .................. C07D 405/04; A61K 31/445
[52] U.S. Cl. ................................ 424/267; 260/293.53
[58] Field of Search ................... 260/293.53; 424/267

[56] References Cited

U.S. PATENT DOCUMENTS

| | | | |
|---|---|---|---|
| 2,985,660 | 5/1961 | Judd et al. | 260/293.53 |
| 3,153,652 | 10/1964 | Drukker et al. | 260/293.53 |
| 3,527,763 | 9/1970 | van der Stelt | 260/293.53 |

OTHER PUBLICATIONS

Chemical Abstracts, 67, 32856h (1967) [Boldo, V. et al., Ann. Chim. (Rome), 56(12), 1603–1613 (1966)].

*Primary Examiner*—Henry R. Jiles
*Assistant Examiner*—Richard A. Schwartz
*Attorney, Agent, or Firm*—Joseph A. Marlino; Richard D. Foggio; William H. Edgerton

[57] ABSTRACT

Tricyclic quinolizidine derivatives administered internally to an animal host, in therapeutically effective amounts, produce antipsychotic activity essentially free of extrapyramidal symptoms.

10 Claims, No Drawings

ANTIPSYCHOTICALLY USEFUL QUINOLIZIDYLIDENE DERIVATIVES OF XANTHENES, THIOXANTHENES AND DIBENZOXEPINS

This invention relates to novel pharmaceutical compositions containing as an active ingredient compounds which produce antipsychotic activity essentially free of extrapyramidal symptoms and to a method of producing antipsychotic activity essentially free of extrapyramidal symptoms which comprises administering nontoxic effective quantities of said active ingredients to an animal. Extrapyramidal symptoms (EPS) are some of the most undesirable and common side effects produced by antipsychotic or neuroleptic drugs. The compounds which are the active ingredients used in the compositions and methods of this invention have a neuropharmacological profile indicative of potent antipsychotic activity but essentially no liability to produce EPS.

The active ingredients used in the compositions and methods of this invention are quinolizidylidene derivatives of xanthenes, thioxanthenes and dibenzoxepins. The compounds of this invention may exist as geometrical isomers, i.e., the bicyclic quinolizidine system may exist as cis or trans isomers depending on the nature of fusion of the two ring systems and in those instances where X is not equal to H additional geometrical isomers are possible depending upon theorientation of the bicyclic ylidene structure. In one of these geometrical isomers the bulk of the tetramethylene fusion to the piperidylidene system is oriented toward the side of the X substitution. The other isomer has the bicyclic bulk directed away from the nuclear substituent X.

It is the intent of this invention to include all possible isomers; however, those in which the bicyclic quinolizidine system is trans are preferred. These isomers may be separated by conventional methods, e.g., recrystallization of the mixture of bases or their acid addition salts or chromatography of the bases.

These isomers are illustrated by the following formulas:

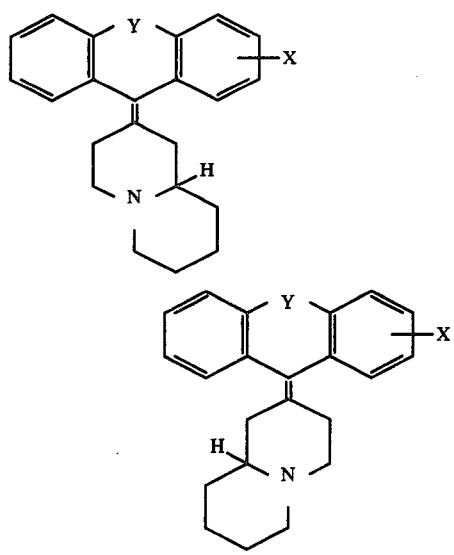

Formula I

Formula II in which:

Y represents oxygen, sulfur or methyleneoxy; and

X represents hydrogen, halogen, thiomethyl cyano, lower alkyl of from 1 to 3 carbon atoms, methoxy, trifluoromethyl, trifluoromethylthio, dimethylaminosulfonyl or acetyl.

The nontoxic pharmaceutically acceptable acid addition salts of the compounds of formulas I and II are similarly useful in the compositions and methods of this invention. Such salts are easily prepared by methods known to the art. The base is reacted with either the calculated amount of organic or inorganic acid in aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, pamoic, succinic, bismethylenesalicylic, acetylsalicylic, methanesulfonic, ethanedisulfonic, acetic, propionic, tartaric, salicylic, citric, gluconic, lactic, malic, mandelic, cinnamic, citraconic, cyclohexylsulfamic, aspartic, stearic, palmitic, itaconic, glycolic, p-aminobenzoic, glutamic, benzenesulfonic and theophyllineacetic acids as well as with 8-halotheophyllines, for example 8-bromotheophylline. Exemplary of such inorganic salts are those with hydrochloric, hydrobromic, sulfuric, phosphoric and nitric acids. Of course, these salts may also be prepared by the classical method of double decomposition of appropriate salts which is well known to the art.

The compounds of formulas I and II are generally prepared from an appropriately substituted xanthone, thioxanthone or dibenzoxepinone by reaction with a quinolizidinyl magnesium halide in an inert organic solvent such as ether, for example ethyl ether, dioxane or tetrahydrofuran, at from room temperature to the reflux temperature of the solvent, for from 30 minutes to 4 hours. The tricyclic carbinol intermediate is dehydrated to the olefin under acid or thermal conditions. Compounds of formulas I and II in which X represents cyano are prepared by treatment of the corresponding derivatives where X is bromo with cuprous cyanide in dimethformamide. Compounds of formula I and II in which X represents acetyl are prepared by addition of a methyl magnesium halide to the cyano compounds followed by aqueous acid hydrolysis of the resulting intermediate.

There is evidence that antipsychotic drugs cause EPS by interfering with neurotransmission in a nigrostriatal dopaminergic pathway. It is throught that they block dopamine receptors in the neostriatum. Therefore, the ability of a drug to block striatal dopamine receptors is a measure of its EPS liability.

To assess the potency of drugs in blocking striatal dopamine receptors a procedure was used which was developed by Ungerstedt [Ungerstedt and Arbuthnott, Brain Res. 24 485 (1970); Ungerstedt, Acta physiol. scand., Suppl. 367, 49 (1971)] using rats with unilateral lesions of the substantia nigra induced by injection of 6-hydroxydopamine. This treatment causes degeneration of the nigrostriatal dopaminergic pathway accompanied by a marked decrease in the dopamine content of the neostriatum on the side of the lesion. Animals with this lesion develop postural and motor asymmetries which are altered by drugs which effect dopaminergic activity. Amphetamine, which releases dopamine and norepinephrine from catecholaminergic neurons, causes these rats to rotate unidirectionally toward the side of the lesion. Since there is a much larger amount of dopamine to be released by amphetamine from the intact nigrostriatal neurons on the non-lesioned side than from those remaining on the lesioned side, the rotational behavior is apparently due to a preponderance of activation of striatal dopamine receptors on the intact side. The ability of a drug to antagonize the rotational behavior is therefore a measure of its ability to block striatal dopamine receptors and is indicative of its potential to produce EPS.

To predict the potential ability of a drug to cause EPS, the ratio of its $ED_{50}$ (i.p.) for antagonism of amphetamine-induced rotation to its $ED_{50}$ (i.p.) for blockage of shock avoidance acquisition in the rat, a procedure for assessing antipsychotic activity, (R/A ratio) is calculated. The $ED_{50}$ values of some clinically established antipsychotics in the avoidance and rotational tests and the R/A ratios are presented in Table I. Chlorpromazine has a R/A ratio of 1.3. Antipsychotics that have a considerably greater propensity to cause EPS than chlorpromazine, e.g., trifluoperazine, haloperidol and pimozide, have ratios of 0.3 to 0.5. The two antipsychotics known to produce EPS to a lesser extent than chlorpromazine, i.e. thioridazine and clozapine, have ratios of 2.7 and 3.8, respectively. Therefore a high R/A ratio predicts that a drug will have a low potential to produce EPS.

Table I

| Drug | A<br>Antagonism of Avoidance Acquisition Rats<br>$ED_{50}$ mg/kg (i.p.) | R<br>Antagonism of Amphetamine-induced Rotation Rats<br>$ED_{50}$ mg/kg (i.p.) | R/A |
|---|---|---|---|
| Chlorpromazine | 1.5 | 2.0 | 1.3 |
| Trifluoperazine | 0.26 | 0.12 | 0.46 |
| Haloperidol | 0.16 | 0.05 | 0.31 |
| Pimozide | 0.24 | 0.08 | 0.30 |
| Thioridazine | 5.1 | 13.7 | 2.7 |
| Clozapine | 6.6 | 25.4 | 3.8 |

Preferred compounds of this invention are the geometrical isomers of 3-(2-chlorothioxanthen-9-ylidene)-quinolizidine. One isomer, having a melting point of 218–220° C., has an $ED_{50}$ of 1.7 mg./kg. (i.p.) for blockade of shock avoidance acquisition and $ED_{50}$ of 8.2 mg./kg. (i.p.) for antagonism of amphetamine-induced rotation resulting in an R/A ratio of 4.8.

The other isomer, which has a melting point of 214°–217° C., has an $ED_{50}$ of 0.7 mg./kg. (i.p.) for blockade of shock avoidance acquisition and an $ED_{50}$ of 2.3 mg./kg. (i.p.) for antagonism of amphetamine induced rotation resulting in an R/A ratio of 3.3.

These R/A ratios indicate that the above noted compounds of this invention are essentially free of EPS liability.

The compositions of this invention are prepared in conventional dosage unit forms by incorporating a compound of formulas I or II or a pharmaceutically acceptable salt thereof, in a nontoxic amount sufficient to produce antipsychotic activity essentially free of extrapyramidal symptoms in an animal, with a nontoxic pharmaceutical carrier according to accepted procedures. Preferably the compositions will contain the active ingredient in an active but nontoxic amount selected from about 1 mg. to about 300 mg., advantageously from about 5 mg. to about 200 mg., of active ingredient per dosage unit.

The pharmaceutical carrier employed may be, for example, either a solid or liquid, giving rise to a wide variety of pharmaceutical forms. If a solid pharmaceutical carrier is used, such as lactose, magnesium stearate, terra alba, sucrose, talc, stearic acid, gelatin, agar, pectin, acacia and the like, the composition can be tableted, used as a pharmaceutical powder, placed in a hard gelatin capsule or in the form of a troche or lozenge. The amount of solid carrier will vary widely but preferably will be from about 25 mg. to about 1 g. If a liquid pharmaceutical carrier is used, such as syrup, peanut oil, olive oil, sesame oil, water and the like, the composition will be in the form of a soft gelatin capsule, syrup, emulsion or a liquid suspension. Similarly the carrier or diluent may include a time delay material such as glyceryl monostearate or glyceryl distearate alone or with a wax.

Parenteral dosage forms such as for intramuscular administration are obtained by dissolving a water soluble salt of the active medicament in water or saline solution in a concentration such that 1 ml. of the solution contains from about 2 mg. to about 50 mg. of active ingredient. The solution can then be filled into single ampuls or multiple dose vials.

In accordance with the method of this invention a compound of formula I or II or a nontoxic acid addition salt thereof is administered internally to an animal in need of antipsychotic activity, preferably with a pharmaceutical carrier, in a nontoxic amount sufficient to produce antipsychotic activity essentially free of extrapyramidal symptoms. The active medicament, preferably in a dosage unit, is administered orally or intramuscularly in an active, nontoxic quantity selected from about 1 mg. to about 300 mg. of the parent chemical of formula I or II. Advantageously equal doses will be administered until a desired effect is obtained, such as two or three times a day. The daily dosage is selected from about 2 mg. to about 900 mg. of active medicament, advantageously from about 10 mg. to about 600 mg. When the method described above is carried out, antipsychotic activity is obtained with minimal EPS.

The following examples illustrate specific compounds, pharmaceutical compositions and their use in accordance with the method of this invention and as such are not to be considered as limitations thereof.

EXAMPLE 1

A solution of 14 g. (0.11 mole) of 3-hydroxyquinolizidine in 75 ml. of thionyl chloride and 50 ml. of benzene was refluxed for one hour. The solvent was completely evaporated, and the residue dissolved in chloroform. The solution was passed through an alumina column and evaporation of the chloroform gave crude 3-chloroquinolizidine. The crude material was chromatographed on an alumina column eluting with ether-petroleum ether, 1:19 to yield pure 3-chloroquinolizidine.

Several drops of ethyl bromide were added to a stirred suspension of 1.29 g. (0.054 g.-atom) of magnesium turnings in 5 ml. of tetrahydrofuran under a nitrogen atmosphere. After the reaction began 9.3 g. (0.054 mole) of 3-chloroquinolizidine in 100 ml. of tetrahydrofuran was added. After the addition was completed the mixture was stirred and refluxed for one hour and cooled to 0° C. To the chilled suspension of the Grignard reagent was added a solution of 12.55 g. (0.051 mole) of 2-chloro-9-thioxanthone in 300 ml. of tetrahydrofuran. The solution was stirred at 24° C. for two hours, poured into aqueous ammonium chloride and extracted with ether. The extracts were washed with water, dried and evaporated to give 2-chloro-9-(3-quinolizidinyl)-9-hydroxythioxanthene.

A solution of 13.2 g. (.034 mole) of 2-chloro-9-(3-quinolizidinyl)-9-hydroxythioxanthene in 100 ml. of concentrated hydrochloric acid was refluxed for three hours. The hydrochloric acid was evaporated, the residue taken up in water, basified with 2 N sodium hydroxide and extracted with ether. The extracts were dried and evaporated. The residue was chromatographed on an alumina column and eluted with ether-chloroform, 1:19. Evaporation of the solvent from the first fraction gave a mixture of geometrical isomers of 3-(2-chlorothioxanthene-9-ylidine)quinolizidine. Thin layer chromatography analysis showed two compounds with very close $R_f$ values.

Fractional crystallization of the mixture of isomers from acetonitrile and then ethanol gave crystals of one isomer. The mother liquors upon evaporation and crystallization from acetonitrile and then ethanol gave crystals of another isomer. These partially separated isomers were each converted to their hexamate salts. Recrystallization from ethanol gave isomers of 3-(2-chlorothioxanthen-9-ylidene)quinolizidine hexamate having melting points of 218°–220°, and 214°–217°, respectively.

EXAMPLE 2

Following the procedure of Example 1, the Grignard reagent, quinolizidine-3-magnesium chloride is reacted with:
9-thioxanthone
2-thiomethyl-9-thioxanthone
2-bromo-9-thioxanthone
2-trifluoromethylthio-9-thioxanthone
2-methoxy-9-thioxanthone
2-trifluoromethyl-9-thioxanthone
to yield respectively:
3-(thioxanthen-9-ylidene)quinolizidine
3-(2-thiomethylthioxanthen-9-ylidene)quinolizidine
3-(2-bromothioxanthen-9-ylidene)quinolizidine
3-(2-trifluoromethylthiothioxanthen-9-ylidene)-quinolizidine
3-(2-methoxythioxanthen-9-ylidene)quinolizidine
3-(2-trifluoromethylthioxanthen-9-ylidene)quinolizidine

EXAMPLE 3

A stirred mixture of 3.96 g. (0.01 mole) of 3-(2-bromothioxanthen-9-ylidene)quinolizidine, 2.70 g. (0.015 mole) of cuprous cyanide, 50 mg. of cupric sulfate, 50 mg. of sodium cyanide in 40 ml. of dimethylformamide is heated at reflux temperature for eighteen hours. The cooled reaction mixture is then poured into 200 ml. of 1 M sodium cyanide. The resulting mixture is extracted with ether. After being washed with an aqueous solution of sodium cyanide and water, the ether solution is dried over magnesium sulfate. The dried solution is concentrated. The residual liquid is chromatographed on an alumina column using ether as the eluate. Evaporation of the appropriate fractional eluant gives 3-(2-cyanothioxanthen-9-ylidene)quinolizidine. A solution of the product in ethanol is treated with a molar equivalent of fumaric acid. The resulting crystals are recrystallized from ethanol to give 3-(2-cyanothioxanthen-9-ylidene)quinolizidine fumarate.

EXAMPLE 4

A solution of 3.42 g. (0.01 mole) of 3-(2-cyanothioxanthen-9-ylidene)quinolizidine in 50 ml. of benzene is added to a stirred solution of 0.013 mole of methyl magnesium bromide in 5 ml. of ether and 50 ml. of benzene. The stirred mixture is heated at reflux temperature for two hours, then it is cooled to 10° C. and added slowly to 250 ml. of vigorously stirred ice-water. Excess 3 N hydrochloric acid is added to the stirred mixture. The aqueous layer is separated and then it is made alkaline with 2.5 N sodium hydroxide. The mixture is extracted with ethyl acetate. After being dried over magnesium sulfate, the extracts are concentrated. The residue is chromatographed on an alumina column using ether as the eluate. Evaporation of the appropriate fractional eluant gives 3-(2-acetylthioxanthen-9-ylidene)quinolizidine which is converted to a fumarate salt by treatment with a molar equivalent of fumaric acid in methanol.

EXAMPLE 5

To 160 ml. of chlorosulfonic acid stirring at 0°–5° C. was gradually added 100.5 g. (0.33 mole) of 2-bromobenzoic acid. Stirring was continued as the temperature was allowed to increase to 25° C. The mixture was stirred and refluxed for three hours, then it was cooled and poured into ice-water. The solid was filtered and then washed with cold water until the filtrate was no longer acidic. The solid, thus isolated, was added, in portions, to 200 ml. of a 40% aqueous solution of dimethylamine. After being diluted with 500 ml. of water, the solution was made acidic with 2.5 N hydrochloric acid. Recrystallization of the precipitated solid from aqueous ethanol gave crystals of 2-bromo-5-dimethylaminosulfonylbenzoic acid, m.p. 170°–172° C.

A mixture of 43.5 g. (0.14 mole) of the above acid, 12.8 g. (0.136 mole) of phenol, 19.8 g. (0.35 mole) of potassium hydroxide, 0.7 g. of copper-bronze powder and 300 ml. of n-amyl alcohol was stirred and refluxed azeotropically until no more water was produced. The mixture was cooled, then it was steam distilled (to remove amyl alcohol) and residue was treated with 2.5 N hydrochloric acid to give 2-carboxy-4'-dimethylaminosulfonyldiphenyl ether, m.p. 156°–158° C.

The above diphenyl ether (12.5 g., 0.04 mole) was heated with 150 g. of polyphosphoric acid at 100° C. for one hour. After the mixture was diluted with ice-water the precipitated solid was filtered and washed with 1 N sodium hydroxide. Recrystallization from ethanol afforded crystals of 2-dimethylaminosulfonyl-9-xanthone, m.p. 180°–181° C.

The above xanthone is reacted with the Grignard reagent quinolizidinyl-3-magnesium chloride. Following the procedure of Example 1 yields 3-(2-dimethylaminosulfonylxanthen-9-ylidene)quinolizidine.

EXAMPLE 6

To a stirred suspension of 24.0 g. (0.5 mole) of a 50% dispersion of sodium hydride in mineral oil in 150 ml. of dimethylformamide under nitrogen was added dropwise 50.4 g. (0.5 mole) of 4-methylphenol in 100 ml. of dimethylformamide. The mixture was stirred until the evolution of hydrogen ceased. A solution of 67.1 g. (0.5 mole) of phthalide in 100 ml. of dimethylformamide was added and the mixture was refluxed two hours then stirred at 25° C. for sixteen hours. The mixture was poured into ice-water and acidified. The precipitated solid was filtered, dried and recrystallized from ethanol to give 2-carboxybenzyl 4-methylphenyl ether. The ether (22.6 g., 0.1 mole) was refluxed in dry xylene with a mixture of 65 g. of Super-cel and 65 g. of phosphorus pentoxide for seventeen hours. The reaction mixture was filtered. The filter cake was washed with xylene and ether. The combined filtrates were concentrated to give a solid which was recrystallized from ethanol to afford crystals of 2-methyldibenzo[b,e]oxepin-11-one, m.p. 100°–103° C.

The above oxepinone is reacted with the Grignard reagent quinolizidinyl-3-magnesium chloride. Following the procedure of Example 1 yields 3-(2-methyldibenzo[b,e]oxepin-11-ylidene)quinolizidine.

EXAMPLE 7

| Ingredients | mg. per Capsule |
| --- | --- |
| 3-(2-Chlorothioxanthen-9-ylidene)-quinolizidine hexamate | 100 |
| Magnesium Stearate | 2 |
| Lactose | 200 |

The above ingredients are mixed, passed through a No. 40 mesh screen, remixed and filled into No. 2 capsules.

| Ingredients | mg. per Tablet |
| --- | --- |
| 3-(2-methoxythioxanthen-9-ylidene)-quinolizidine | 100 |
| Calcium Sulfate, dihydrate | 125 |
| Sucrose | 25 |
| Talc | 5 |
| Stearic acid | 3 |

The sucrose, calcium sulfate and quinolizidine are thoroughly mixed and granulated with hot 10% gelatin solution. The wetted mass is passed through a No. 6 standard mesh screen onto drying trays. The granules are dried at 120° F. and passed through a No. 20 mesh screen. These granules are then mixed with starch, talc and stearic acid, passed through a No. 60 mesh screen and then compressed into tablets.

What is claimed is:

1. A chemical compound of the formula:

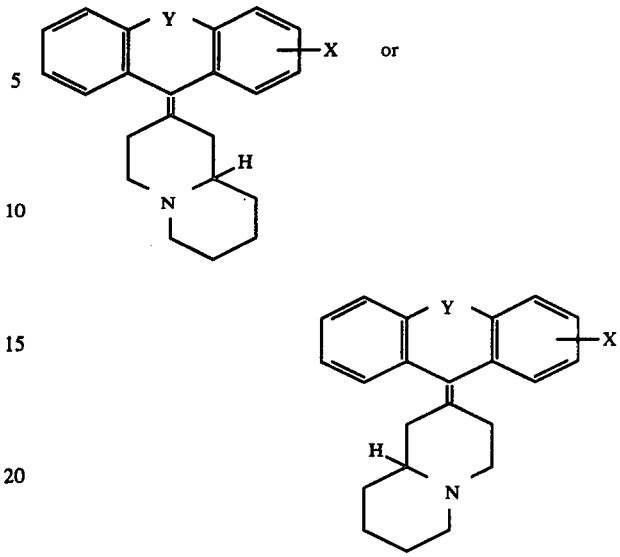

or a pharmaceutically acceptable acid addition salt thereof in which:
Y is oxygen, sulfur or methyleneoxy; and
X is hydrogen, halogen, thiomethyl, cyano, lower alkyl of from 1 to 3 carbon atoms, methoxy, trifluoromethyl, trifluoromethylthio, dimethylaminosulfonyl or acetyl.

2. A chemical compound of claim 1 in which Y is sulfur.

3. A chemical compound of claim 2 in which X is halogen.

4. A chemical compound of claim 3 in which X is chloro.

5. A pharmaceutical composition having antipsychotic activity essentially free of extrapyramidal symptoms in dosage unit form which comprises a pharmaceutical carrier and an antipsychotically effective amount of a compound according to claim 1 or a nontoxic pharmaceutically acceptable acid addition salt of said compound.

6. A pharmaceutical composition according to claim 5 in which the compound is 3-(2-chlorothioxanthen-9-ylidene)quinolizidine.

7. A pharmaceutical composition according to claim 5 in which the active ingredient is in an amount of from about 1 mg. to about 300 mg. per dosage unit.

8. A method of producing antipsychotic activity essentially free of extrapyramidal symptoms which comprises administering internally to an animal host in need of such activity a therapeutically effective amount of the compound of claim 1 or a nontoxic pharmaceutically acceptable acid addition salt thereof.

9. A method according to claim 8 in which the compound is 3-(2-chlorothioxanthen-9-ylidene)quinolizidine.

10. A method according to claim 8 in which said compound is administered in a daily dose of from about 2 mg. to about 900 mg.

* * * * *